United States Patent
Levine et al.

(10) Patent No.: US 8,082,036 B2
(45) Date of Patent: *Dec. 20, 2011

(54) AUTOMATIC SIGNAL AMPLITUDE MEASUREMENT SYSTEM IN THE SETTING OF ABNORMAL RHYTHMS

(75) Inventors: Paul A. Levine, Santa Clarita, CA (US); Amdt Godau, Los Angeles, CA (US)

(73) Assignee: Pacesetter, Inc., Sylmar, CA (US)

( * ) Notice: Subject to any disclaimer, the term of this patent is extended or adjusted under 35 U.S.C. 154(b) by 469 days.

This patent is subject to a terminal disclaimer.

(21) Appl. No.: 12/266,441

(22) Filed: Nov. 6, 2008

(65) Prior Publication Data

US 2009/0082826 A1  Mar. 26, 2009

Related U.S. Application Data

(62) Division of application No. 11/166,618, filed on Jun. 24, 2005, now Pat. No. 7,463,926.

(51) Int. Cl.
*A61N 1/37* (2006.01)

(52) U.S. Cl. ............... 607/27; 600/509; 600/515

(58) Field of Classification Search ............ 607/27, 607/28; 600/509, 513, 515–519, 521
See application file for complete search history.

(56) References Cited

U.S. PATENT DOCUMENTS

| | | | |
|---|---|---|---|
| 5,269,300 A | 12/1993 | Kelly et al. | |
| 5,365,932 A | 11/1994 | Greenhut | |
| 5,374,282 A | 12/1994 | Nichols et al. | |
| 5,564,430 A | 10/1996 | Jacobson et al. | |
| 5,755,738 A | 5/1998 | Kim et al. | |
| 5,957,857 A * | 9/1999 | Hartley | 600/509 |
| 6,029,086 A | 2/2000 | Kim et al. | |
| 6,112,119 A | 8/2000 | Schuelke et al. | |
| 6,249,701 B1 | 6/2001 | Jajasekhar et al. | |
| 6,266,565 B1 | 7/2001 | Er et al. | |
| 6,311,089 B1 | 10/2001 | Mann et al. | |
| 6,418,343 B1 | 7/2002 | Zhang et al. | |
| 6,477,406 B1 * | 11/2002 | Turcott | 600/518 |
| 6,508,327 B1 | 1/2003 | Thornton | |
| 6,539,259 B1 | 3/2003 | Weinberg et al. | |
| 6,594,523 B1 | 7/2003 | Levine | |
| 2002/0165587 A1 | 11/2002 | Zhang et al. | |
| 2004/0243014 A1 * | 12/2004 | Lee et al. | 600/509 |
| 2005/0004486 A1 * | 1/2005 | Glass et al. | 600/515 |

FOREIGN PATENT DOCUMENTS

| | | |
|---|---|---|
| EP | 0581010 A2 | 2/1994 |
| EP | 0581010 A3 | 2/1994 |
| EP | 0958843 A1 | 11/1999 |
| WO | 9965565 A1 | 12/1999 |
| WO | 0047277 A1 | 8/2000 |
| WO | 0124877 A1 | 4/2001 |

* cited by examiner

*Primary Examiner* — Carl H Layno
*Assistant Examiner* — Eugene Wu

(57) ABSTRACT

A system for automatically evaluating the sensing and detection of physiological processes by an implantable medical device, such as an implantable cardiac stimulation device. The system includes an automatic testing algorithm which iteratively adjusts at least one of the threshold and gain settings of the device and evaluates the accuracy of the detection for refining the programming of the device. The algorithm can include sampling the physiological process beginning at a relatively low rate to avoid excessive burden on the processing and battery capacity available and progressively increasing the rate to obtain higher resolution data. The algorithm can also evaluate the observed physiological process for periodicity and can determine repetition of an irregular pattern, such as bigeminy, and use the determined pattern for predictive purposes to refine the programming of the device. The algorithm employs observation of a change in observed pattern as indicia for loss of proper detection.

10 Claims, 19 Drawing Sheets

AUTOMATIC SIGNAL AMPLITUDE MEASUREMENT SYSTEM IN THE SETTING OF ABNORMAL RHYTHMS

CROSS REFERENCE TO RELATED APPLICATIONS

This application is a division of U.S. patent application Ser. No. 11/166,618, filed Jun. 24, 2005, titled "Automatic Signal Amplitude Measurement System in the Setting of Abnormal Rhythms", now U.S. Pat. No. 7,463,926.

FIELD OF THE INVENTION

The invention relates to the field of implantable medical devices and more particularly to devices and algorithms for automatically evaluating and adjusting sensing for improved detection, particularly of irregular waveforms.

BACKGROUND OF THE INVENTION

Many implantable medical devices include among their operation the sensing and detection of one or more physiological parameters. Such devices may include one or more implantable sensing electrodes and typically include corresponding signal amplifier and sensing circuits. As used herein, "sensing" refers to developing a signal (such as an electrical potential) corresponding to one or more physiological parameters and the sensing can occur continuously and/or on a periodic or sampled basis. "Detection" refers to the determination of the sensed signal as corresponding to the occurrence or lack thereof of a given physiological process.

Some difficulties faced with accurately sensing and detecting physiological processes, such as with an implantable medical device, include that many physiological parameters of interest generate relatively low level base signals and are frequently presented in a background of relatively wide band noise which may be of greater magnitude than the signals of the physiological process of interest. A further difficulty is that a physiological process of interest may be of irregular or intermittent nature thus complicating accurate detection, e.g. whether a given physiological process is absent, delayed, premature, or of smaller magnitude than expected. For one example, implantable cardiac stimulation devices such as pacemakers and/or cardioverter defibrillators (ICDs) automatically sense the patient's cardiac activity by deriving electrical signals from the electrochemical activity of the heart, use these sensed signals to detect the presence/absence, magnitude of, and relative timing of activity in cardiac tissue and automatically supply therapeutic electrical stimulation as indicated to provide desired cardiac rhythm.

In implantable medical devices, such as pacemakers and ICDs, electrical signals picked up by one or more sensing electrode in contact with the patient's cardiac tissue is conducted by one or more leads to battery powered sensing circuitry typically contained within a hermetically sealed biocompatible housing or can which is also implanted within the patient. The sensing circuitry typically includes variable gain amplifier and detection circuitry which evaluates the amplified signals sensed from the patient's cardiac tissue for determination of presence and timing of cardiac activity of interest. A threshold is typically set such that sensing of a cardiac signal within a given time window and above the threshold constitutes "detection" of the corresponding physiological process, such as an atrial or ventricular contraction. The gain of the amplifier and the setting of the threshold is preferably set such that the device accurately senses and detects cardiac activity occurring with reduced incidence of failure to detect such activity (undersensing) as well as reduced incidence of falsely "detecting" signals as corresponding to a physiological process not actually present (oversensing). However, such setting of the gain and thresholds is complicated by the variable timing and magnitudes of the signals of interest particularly in patients for whom implantation of a cardiac stimulation device is indicated.

A variety of devices and algorithms are known which attempt to more accurately determine and set appropriate gain and threshold settings for an implantable medical device and patient combination. Such devices and algorithms may operate automatically within the device itself and/or may operate in a command manner via an external device in communication with the implantable device, such as a physician's programmer. Setting and evaluation of amplifier gains and thresholds may occur at initial implantation as well as periodically throughout the implant lifetime.

For example, one process for setting the sensing thresholds involves establishing communication between an implantable cardiac stimulation device and an external physician's programmer. A clinician then commands, via the physician's programmer, the implantable device to progressively program itself to less sensitive settings. The performance of the implantable device with the progressively less sensitive settings is evaluated with respect to independent measurement of the patient's cardiac activity via a surface electrocardiogram (ECG) and loss of sensing is recognized by either competition between intrinsic and paced activity or failure of the device to indicate an appropriate sense marker despite visible observation of the native signal by the surface ECG. The clinician would terminate the test and use this data to then program the most appropriate threshold settings. A refinement of this general process is also known wherein, upon initiation of the test, the test proceeds automatically with communication between the programmer and the implantable device. However, these processes are subject to misinterpretation leading to instances of suspect results which will be discussed in greater detail below.

One theoretically possible remedy for more accurately conducting sensing measurement tests, such as sensing of the P and R waves of a patient's cardiac cycle, is to perform relatively high frequency sampling of the wave forms to much more accurately obtain information relating to the magnitude and timing of these physiological signals. However, in practical application, this has not proven a viable possibility. Firstly, the microprocessor and memory resources of the implantable device are limited in capacity and the allocation of the necessary processing resources to support very high rate sampling has not proven feasible. Secondly, relatively high rate sampling is also relatively demanding of the limited energy capacity of the battery and thus employing high rate sampling, particularly on a periodic basis to re-verify or adjust sensing threshold throughout the implantation period unacceptably drains the battery indicating an early invasive procedure to replace the battery.

Thus, from the forgoing it will be appreciated that there is a need for a system that can more accurately determine appropriate sensing threshold parameters in an implantable medical device, such as in an implantable cardiac stimulation device, to facilitate more accurate detection of physiological processes of interest. There is a particular need for a system of setting such sensing threshold parameters in applications where the subjects' physiological processes generate indicia that are irregular in nature over time. It would be further advantageous for such a system to be provided in a manner that is substantially automated to reduce operating burden on clinicians or other users of the system.

SUMMARY

Preferred embodiments provide a system and method for automatically testing the measurement of one or more physiological processes by an implantable medical device. The sensing of the physiological process is evaluated and a pattern of the process is determined, such as a regular periodicity or a repetition of an irregular complex. The determined pattern can be used for predictive purposes. For example, in one embodiment, a more aggressive set of sensing parameters is iteratively temporarily set and the pattern is redetermined until a change in the pattern indicates that the more aggressive set of sensing parameters has led to at least a partial loss of detection. The system can store the information and report this result for evaluation by a clinician and/or can use the result for possible refinement of the programmed sensing parameters.

DETAILED DESCRIPTION OF THE PREFERRED EMBODIMENT

Reference will now be made to the drawings wherein like numerals refer to like parts throughout. The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
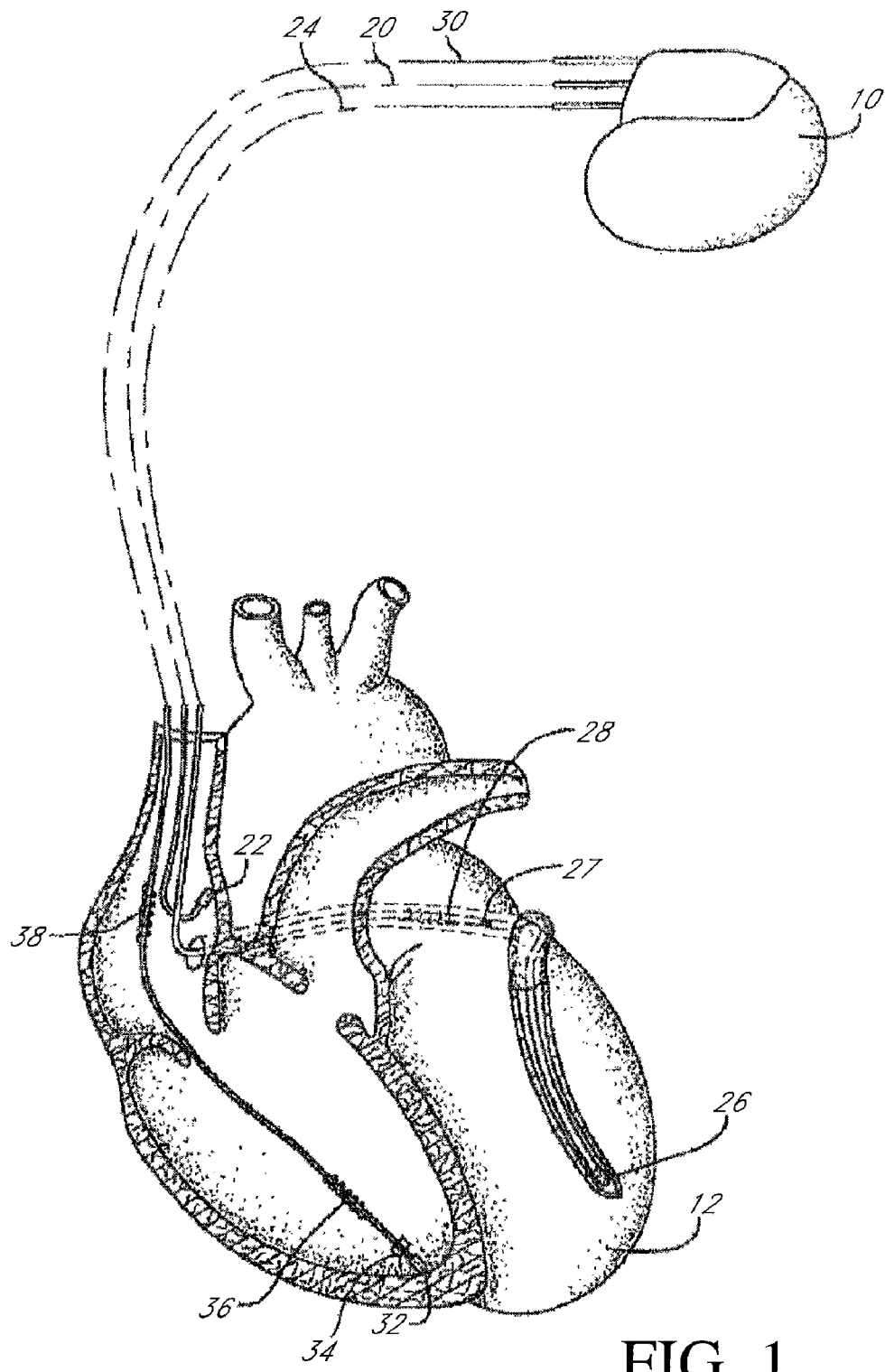
FIG. 1 is a simplified diagram illustrating an implantable stimulation device in electrical communication with at least three leads implanted into a patient's heart for delivering multi-chamber stimulation and shock therapy.

In one embodiment, as shown in FIG. 1, a device 10 comprising an implantable cardiac stimulation device 10 is in electrical connection with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium (OS) for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical connection with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
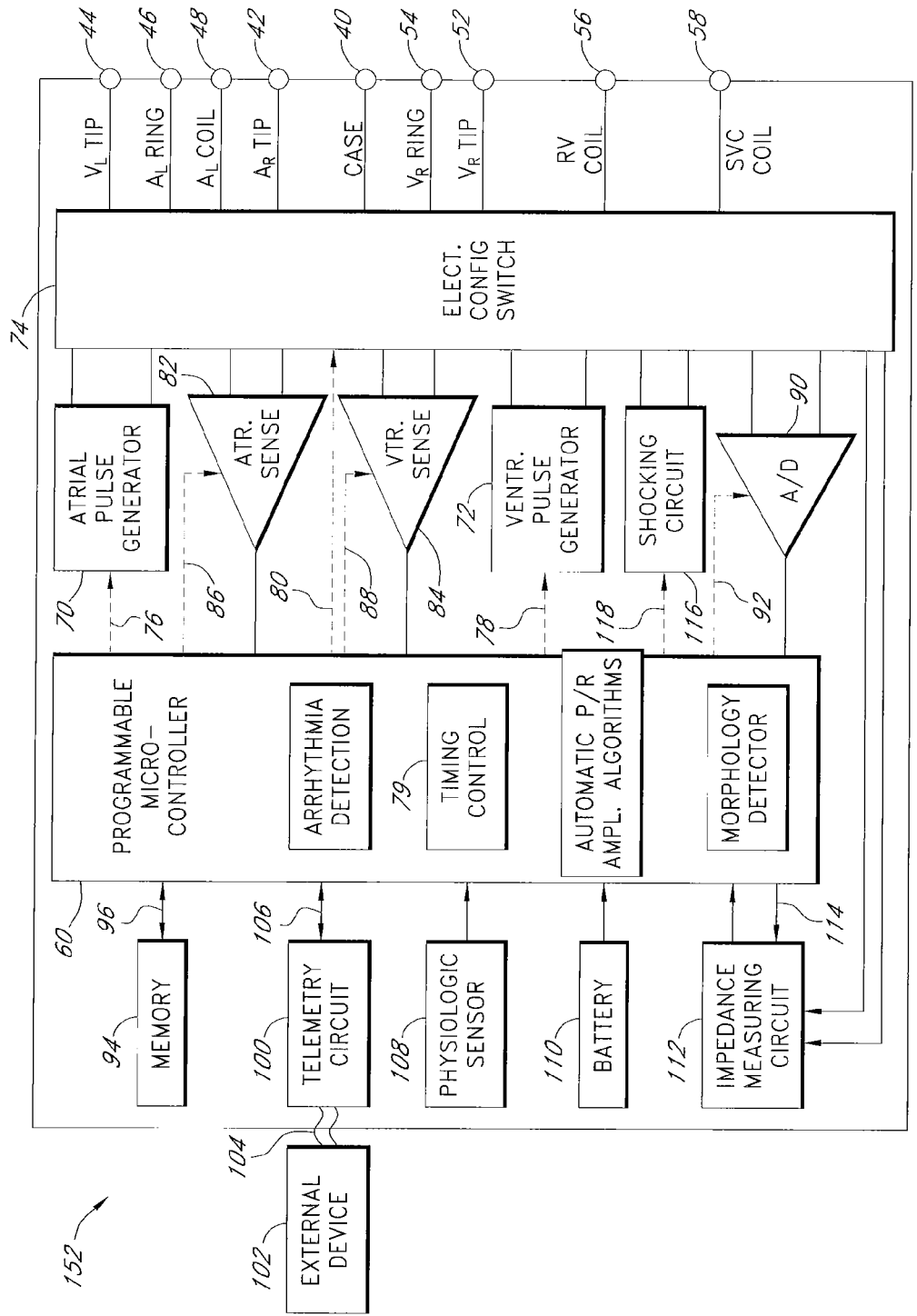
FIG. 2 is a functional block diagram of a multi-chamber implantable stimulation device illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independently of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "diagnosis" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) system 90. The A/D system 90 is configured to acquire intracardiac electrogram (IEGM) signals and convert the raw analog data into a digital signal. The digital signals can then be stored, in certain embodiments in memory 94, for later processing and/or telemetric transmission to an external device 102. The A/D system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia diagnosis criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows IEGMs and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices.

As further shown in FIG. 2, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5-10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3A:
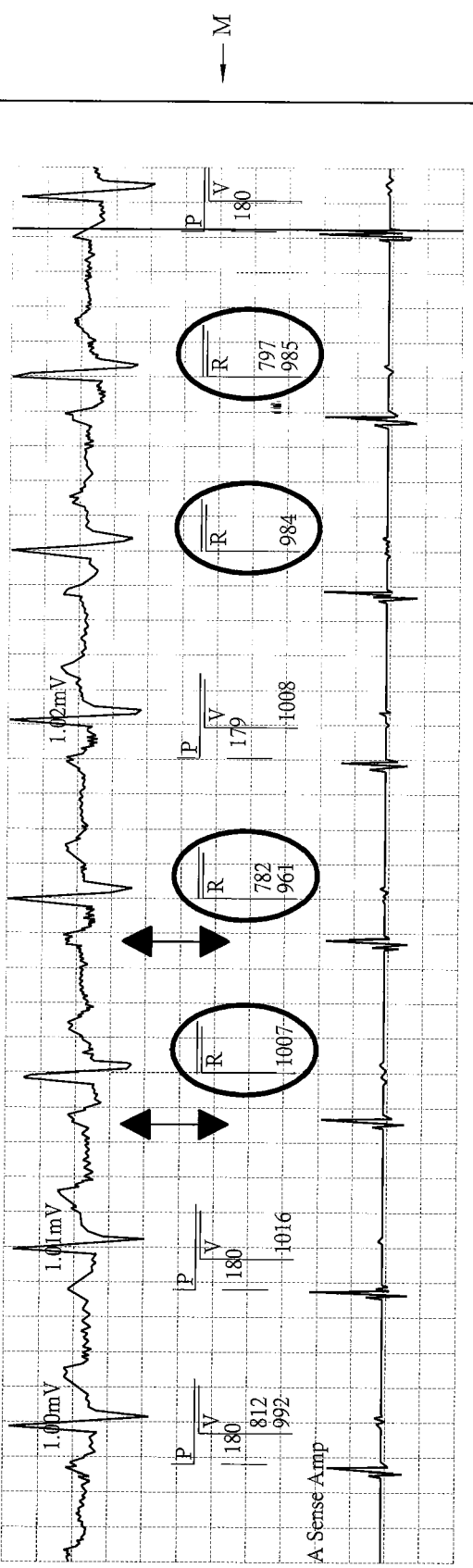
FIGS. 3A-3B and 4A-4B are exemplary screen shots from a physician's programmer reporting results of P wave sensing measurement test results.
Figure 3B:
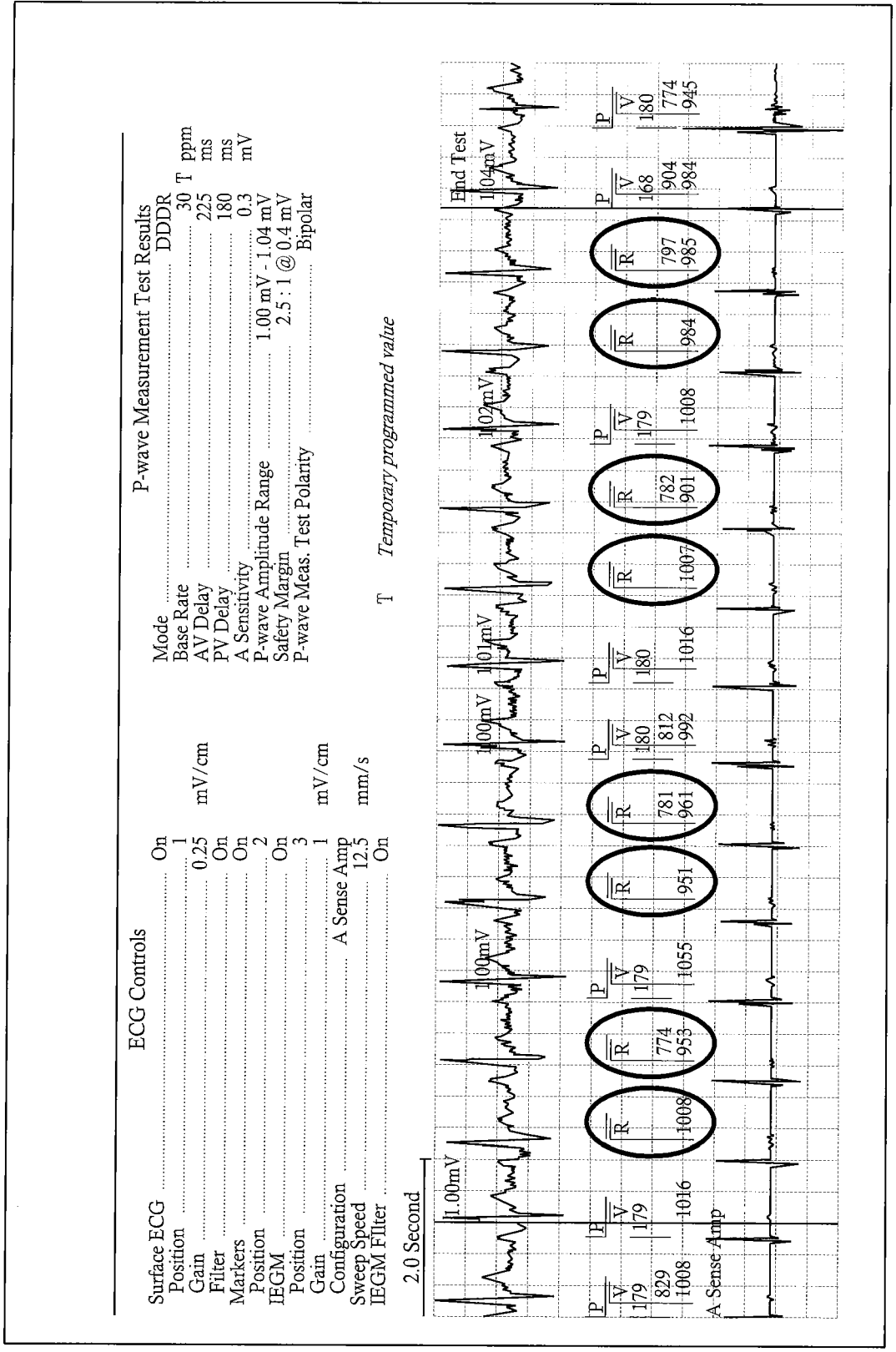

FIGS. 3A and 3B are example screen shots from the external device 102 in this embodiment comprising a physician's programmer in communication with the device 10. FIG. 3A illustrates in greater detail and FIG. 3B along a longer time scale difficulties in accurately setting sensing thresholds for the device 10 addressed by embodiments of the invention. FIGS. 3A and 3B illustrate the progression of a P wave measurement test and the results thereof. As can be seen in FIG. 3A, in this embodiment, the atrial sensitivity is set to 0.3 millivolts and for the first two cycles returns appropriate markers M for the sensed cardiac events. The markers M appropriately indicate detection of P and R waves and the respective observed values or alternatively the delivery of atrial (A) and/or ventricular (V) pacing. However, for the third and fourth as well as sixth and seventh cycles, the markers M (circled) fail to indicate detection of the P wave for that cycle (indicated also by the double arrows) or delivery of an atrial pacing pulse, although the activity is discernable on the surface ECG trace. However, the automated test fails to indicate this failure to detect and reports a P wave amplitude range of 1.00 to 1.04 millivolts. Thus, while the automated test fails to indicate the suspect validity, it is apparent that completely accurate detection is not occurring in this embodiment.

Figure 4A:
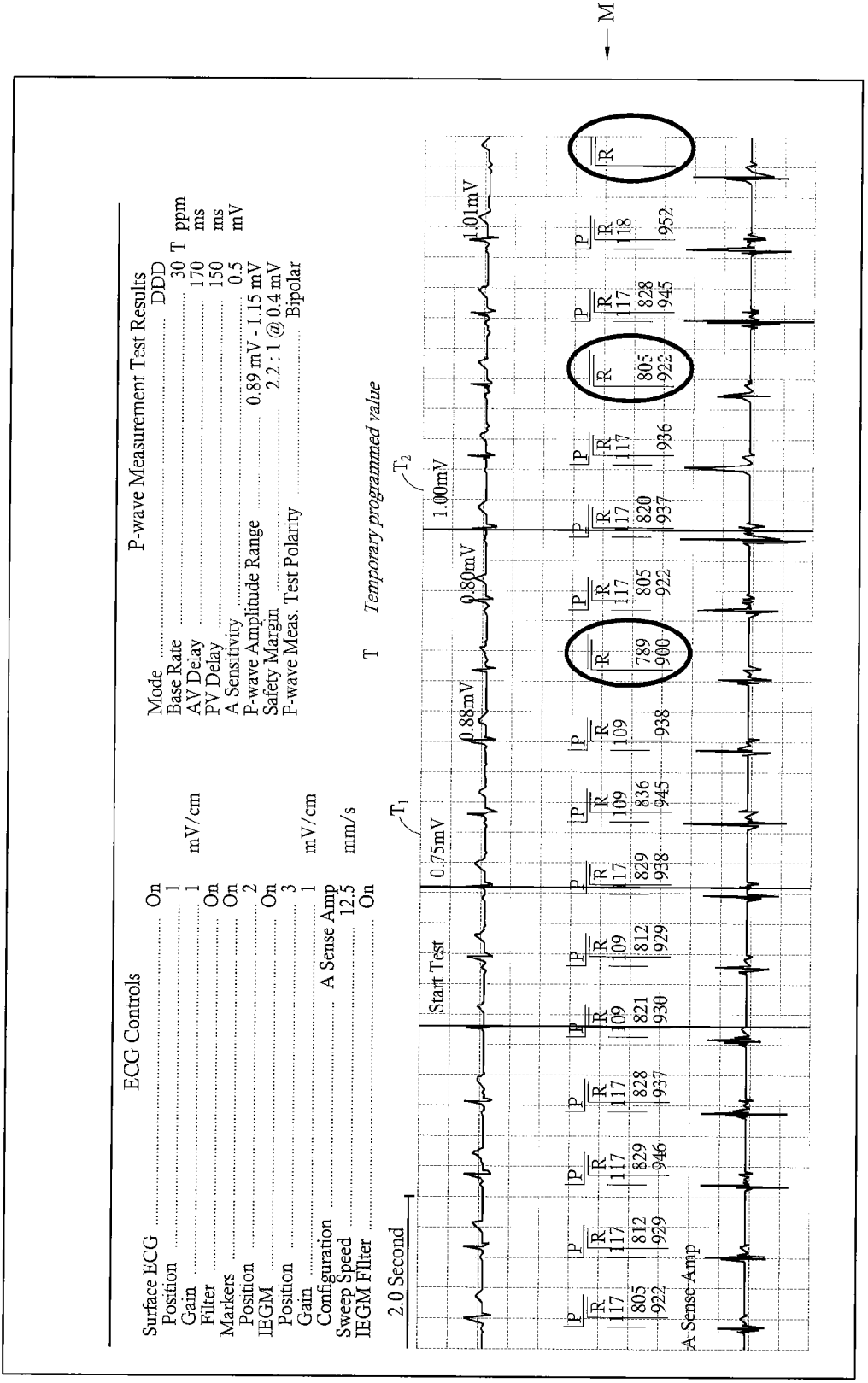
Figure 4B:
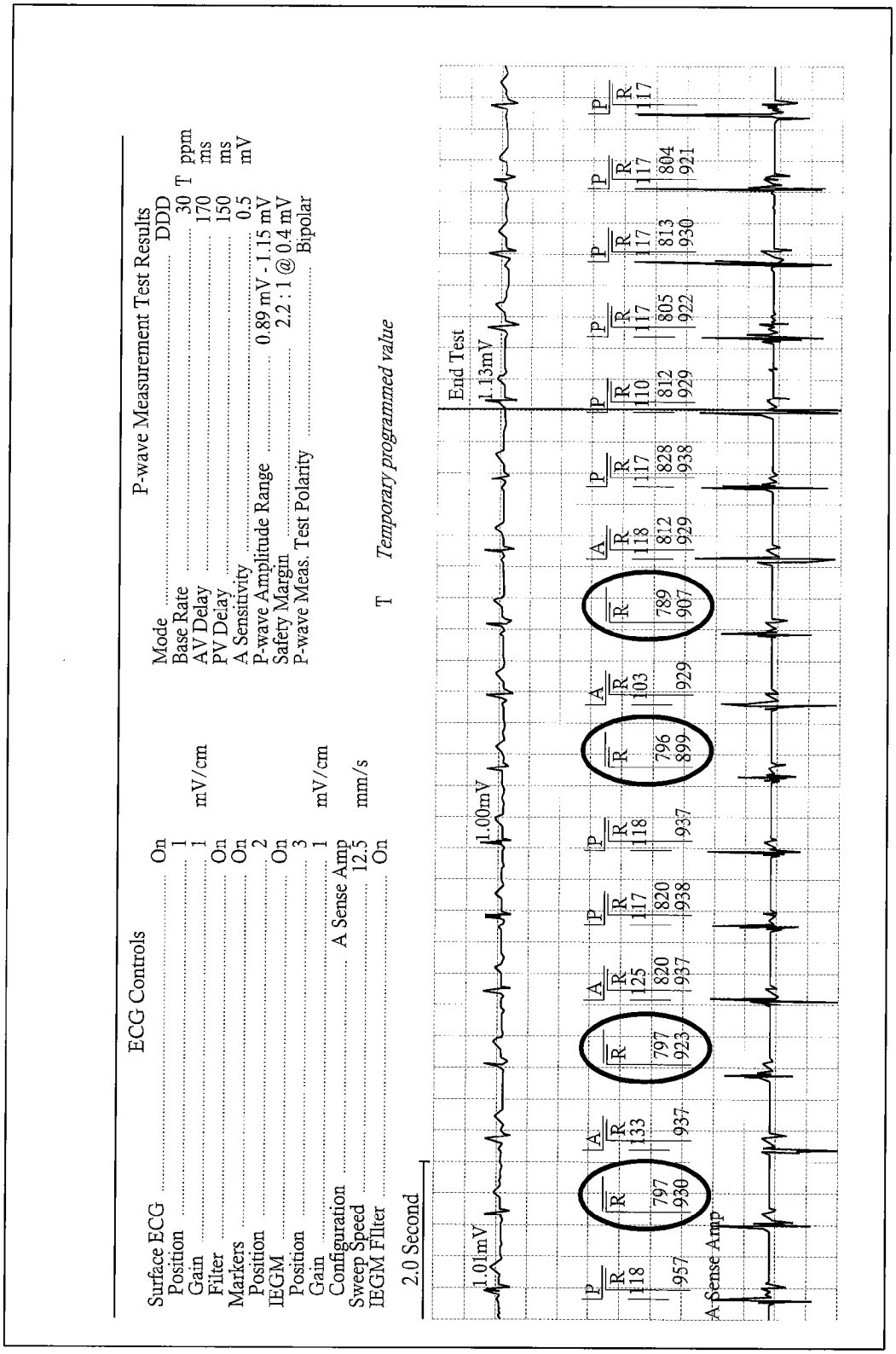

FIGS. 4A and 4B illustrate a similar P wave measurement test which begins with an atrial sensitivity of 0.5 millivolts and which increments to a first higher test threshold $T_1$ of 0.75 millivolts and then to a second yet higher test threshold $T_2$ of 1.0 millivolts. For the duration of the test performed with atrial sensitivity set at 0.5 millivolts, the markers M indicate that appropriate detection does occur. However, as the atrial sensitivity in incremented to $T_1$ (0.75 millivolts), there is a single incidence of failure to accurately detect a P wave and as the sensitivity is further incremented to $T_2$ (1.0 millivolts), more numerous failures to accurately detect the P waves occur as further illustrated in FIG. 4B (again indicated by a discernable ECG trace and the absence of a corresponding sense marker (circled)). Again, in this embodiment a result was reported indicating a P wave amplitude range of 0.89 millivolts to 1.15 millivolts, however the results of these tests are also highly suspect.

Figure 5:
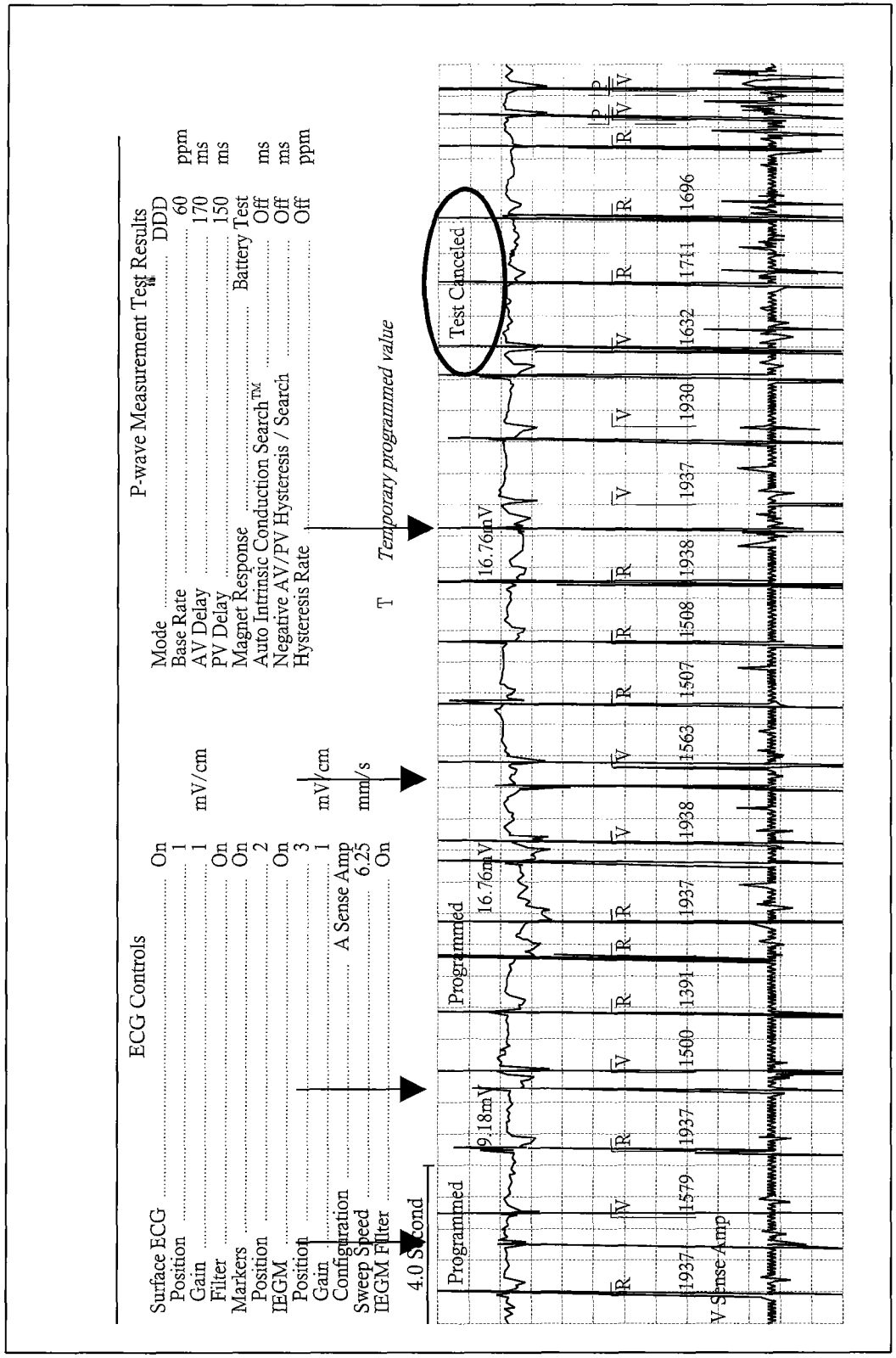
FIG. 5 is an example screen shot of a physician's programmer reporting results of an R wave sensing measurement test.

FIG. 5 illustrates an R wave amplitude measurement test that was cancelled in progress as when the least sensitive setting (gain) was reached, consistent detection of the signal was not occurring and thus ventricular pacing pulses (V) began to be delivered. As indicated by the downward arrows, this also occurred at more sensitive settings identified by these arrows.

Figure 6A:
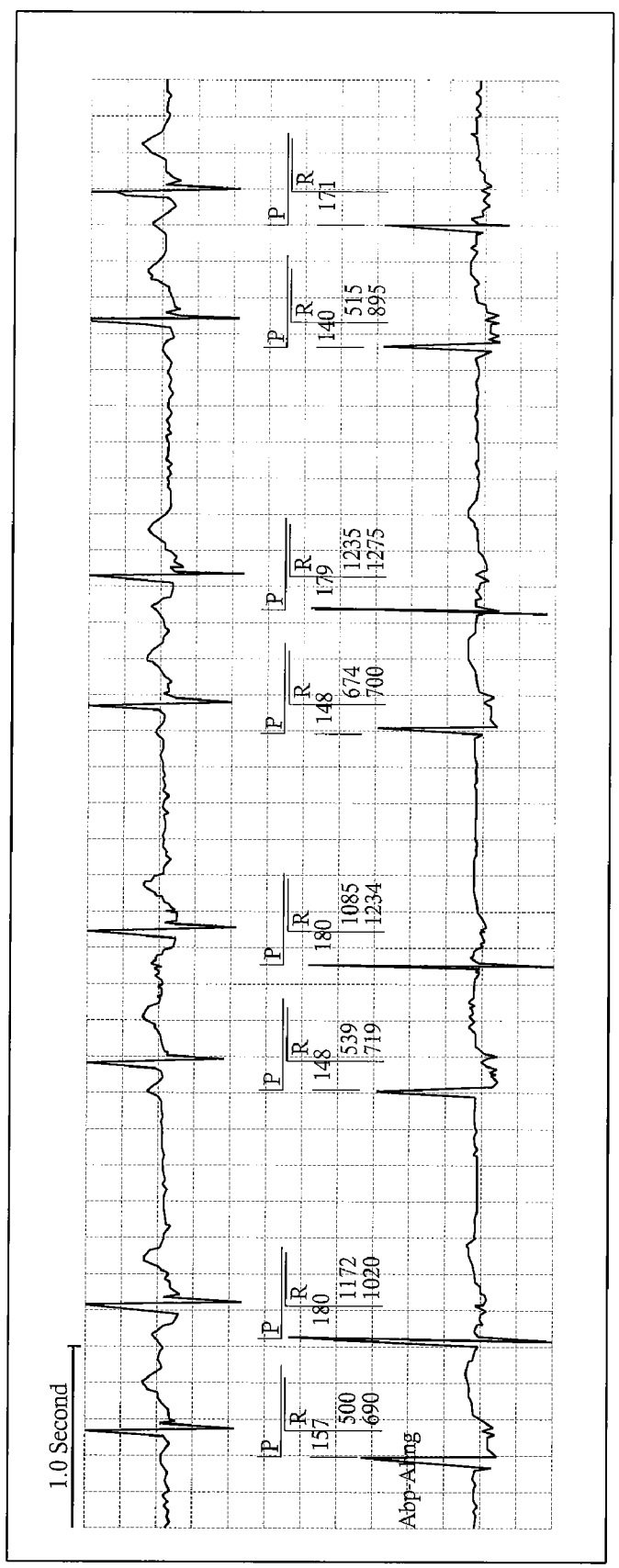
FIGS. 6A-6C are exemplary close ups from screen shots of a physicians programmer reporting results of automatic P wave sensing measurement tests and illustrating a condition of atrial bigeminy.
Figure 6B:
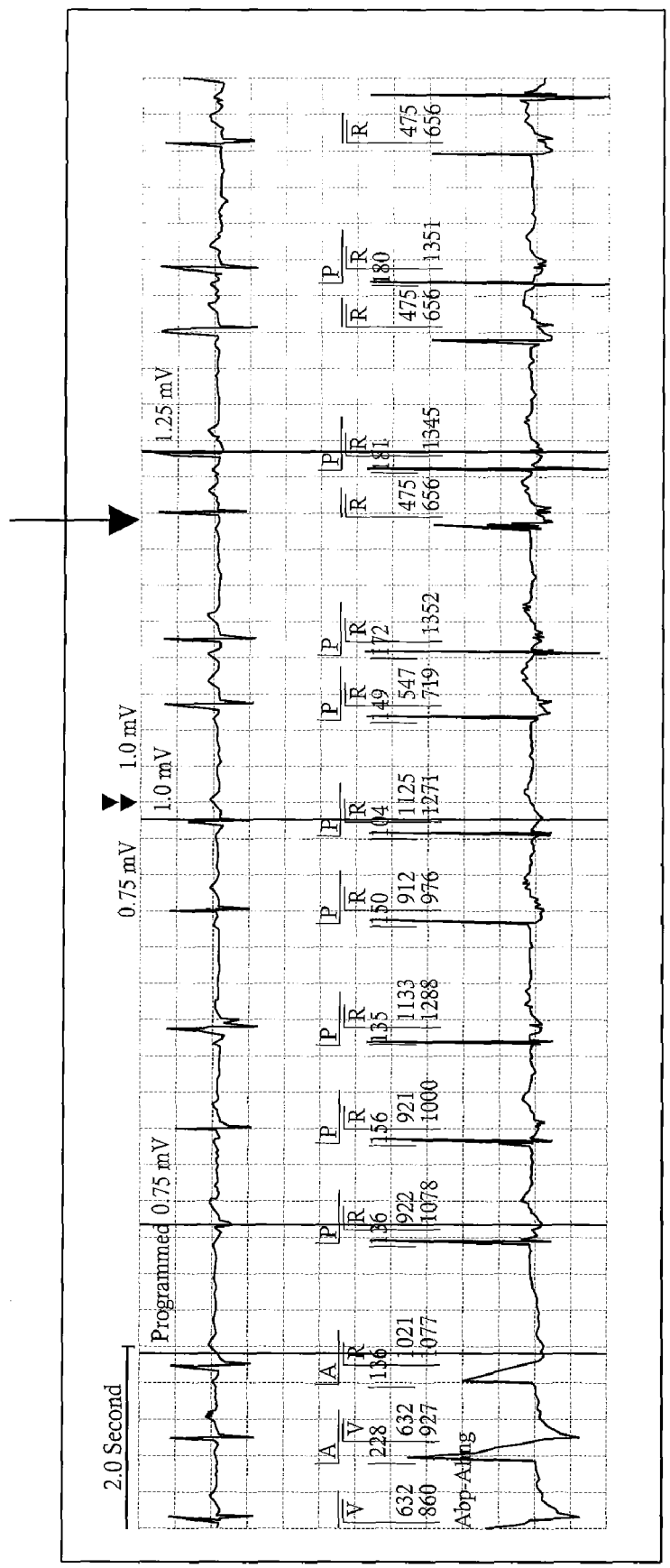
Figure 6C:
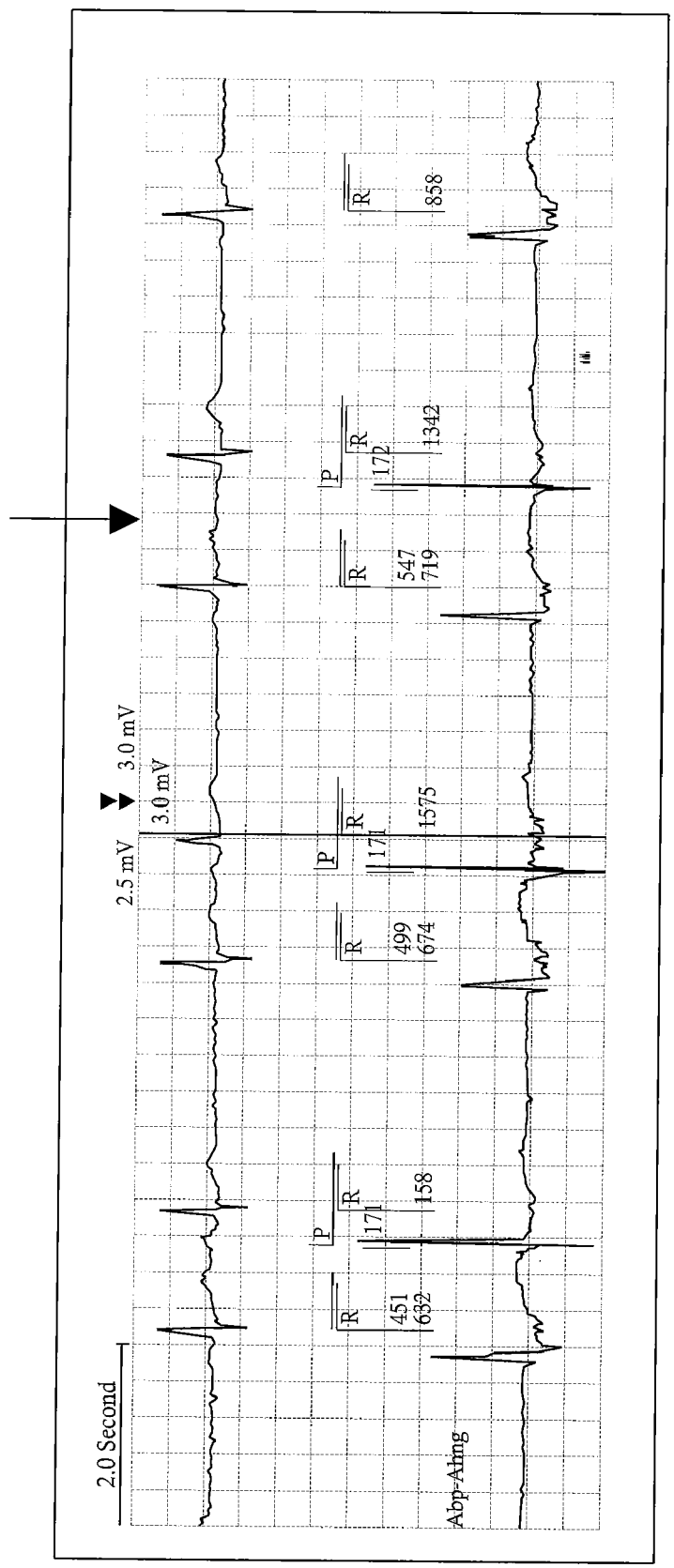

FIGS. 6A-6C illustrate yet other embodiments of physiological parameters which present difficulties in accurately sensing and detecting but which are also addressed by the invention as described in greater detail below. FIG. 6A illustrates a patient condition of atrial bigeminy characterized by a relatively regular repetition of paired atrial beats or a cardiac rhythm with alternating short and long intervals between each atrial event. The figure also illustrates the sensed reading from a standard bipolar intracardiac electrogram (IEGM) between the $A_{TIP}$ and $A_{RING}$ electrodes. It can be seen that these two complexes of the bigeminous pair have distinctly different amplitudes.

FIG. 6B illustrates the results returned from a semi-automatic threshold test and show that with the threshold set at 1.0 millivolts, there is intermittent failure to detect the first P wave of the bigeminous pair as indicated by the downwards arrow. FIG. 6C illustrates a continuation of the semi-automatic sensing threshold test of FIG. 6B and shows that there continues to be intact sensing for the second complex of the pair up to at least 3.0 millivolts as identified by the P marker aligned with the second P wave of the pair. FIG. 6C also illustrates that there is a visible difference in morphology between the two complexes of the bigeminous pair.

Figure 7:
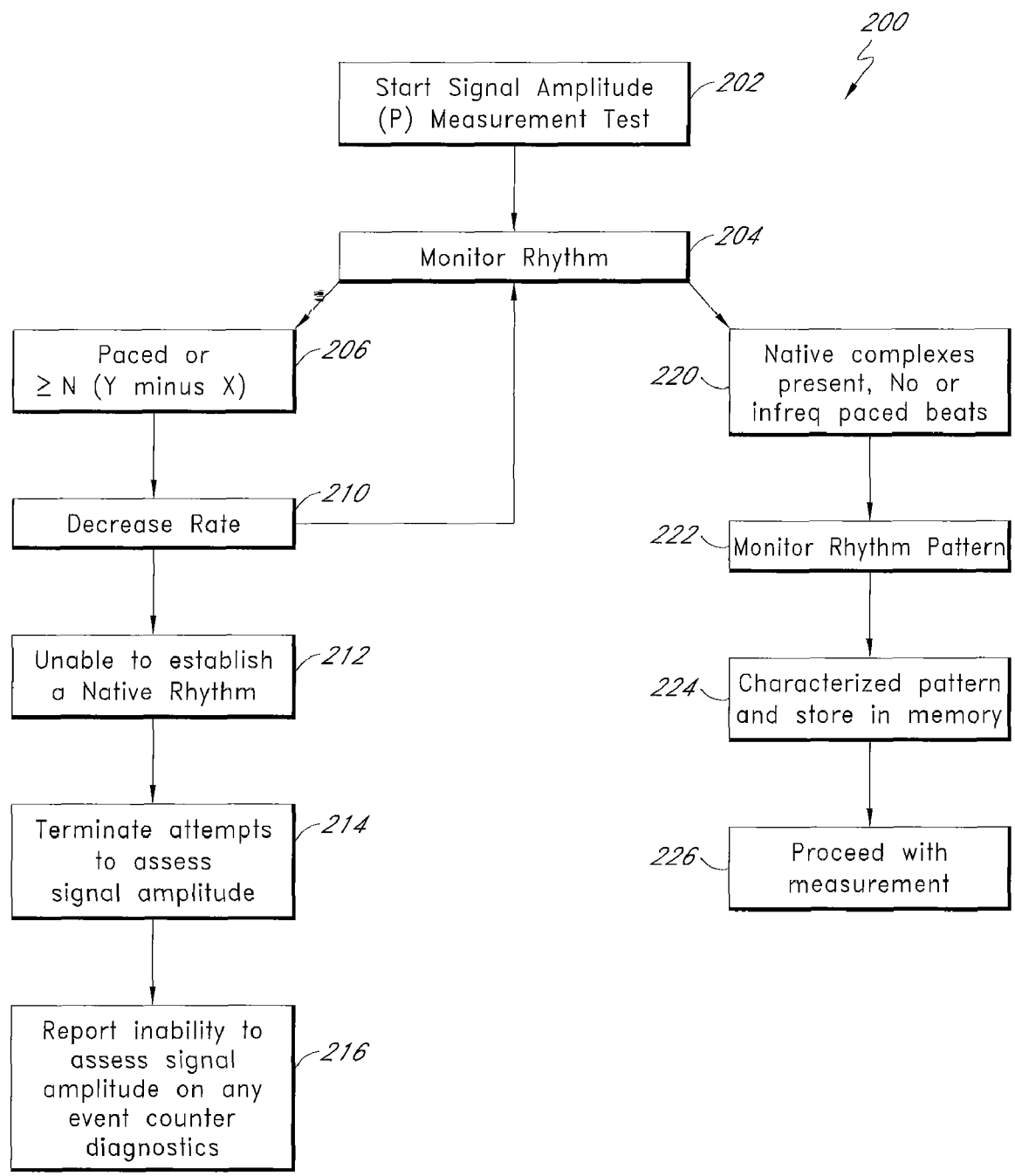
FIG. 7 is a flow chart of one embodiment of an automatic signal amplitude measurement test.

FIG. 7 is a flow chart of one embodiment of an automatic signal amplitude measurement algorithm 200. Beginning in a start state 202, the device 10 proceeds to monitor one or more physiological processes. These physiological processes can include cardiac activity which will be used as an explanatory vehicle herein, however it will be understood that the automatic signal amplitude measurement algorithm 200 as described can be utilized for other physiological parameters of interest depending upon the particular application. In state 204, the physiological process, in this embodiment the cardiac activity, is monitored by the device 10 as previously described. State 204 also includes an evaluation component wherein a determination is made whether the observed activity is intrinsic or corresponds to stimulation from the device 10. A determination is made that the observed activity corresponds to the therapy provided by the device 10 in state 206 if the cardiac activity is paced or if the observed activity constitutes a proportion of paced activity with respect to overall activity greater than or equal to a determined value N.

If the evaluations of states 204 and 206 are affirmative, the device 10 then decreases the base rate at which therapy is provided in state 210 in an attempt to temporarily re-enable intrinsic activity of the heart 12 and the rhythm is re-evaluated in state 204. This process is repeated iteratively until either a defined minimum base rate is reached or a sufficient proportion of intrinsic activity is observed. If the determination of state 206 remains affirmative, e.g. that the intrinsic activity is not restored above the discrimination point of state 206, a state 212 follows wherein it is established that the intrinsic activity cannot be restored at the present time. Then a state 214 would follow where the attempts to automatically measure the signal amplitude are terminated and in state 216 a report would be generated indicating the inability to assess the signal amplitude.

When the determination aspect of state 204 indicates that there exists intrinsic or a sufficiently intrinsic amount of the physiological activity being sensed in a state 220, a state 222 follows wherein the physiological process is evaluated on an ongoing basis.

A particular embodiment of the invention includes this evaluation of state 222 of monitoring the sensed physiological parameter(s) especially for observation of relatively predictable patterns of activity. For example, as illustrated in FIGS. 6A-6C, a bigeminous condition of a relatively regular repetition of paired cycles or a alternating pattern of relatively short and long intervals between otherwise regular events demonstrates a pattern of regular irregularity. Thus, the evaluation of state 222 includes monitoring for a pattern of physiological activity that is not strictly periodic, however does exhibit the characteristic of a repetition of a more complex pattern, such as bigeminy, trigeminy, etc. Thus, upon determination of a particular pattern to the physiological activity made in state 222, the algorithm 200 can use this determination for predictive purposes.

Following the monitoring of state 222, the algorithm can characterize any determined pattern and store such a pattern and characterization in memory in state 224. With the predictive capabilities of one or more determined patterns, the algorithm proceeds with a signal amplitude measurement in state 226.

Figure 8:
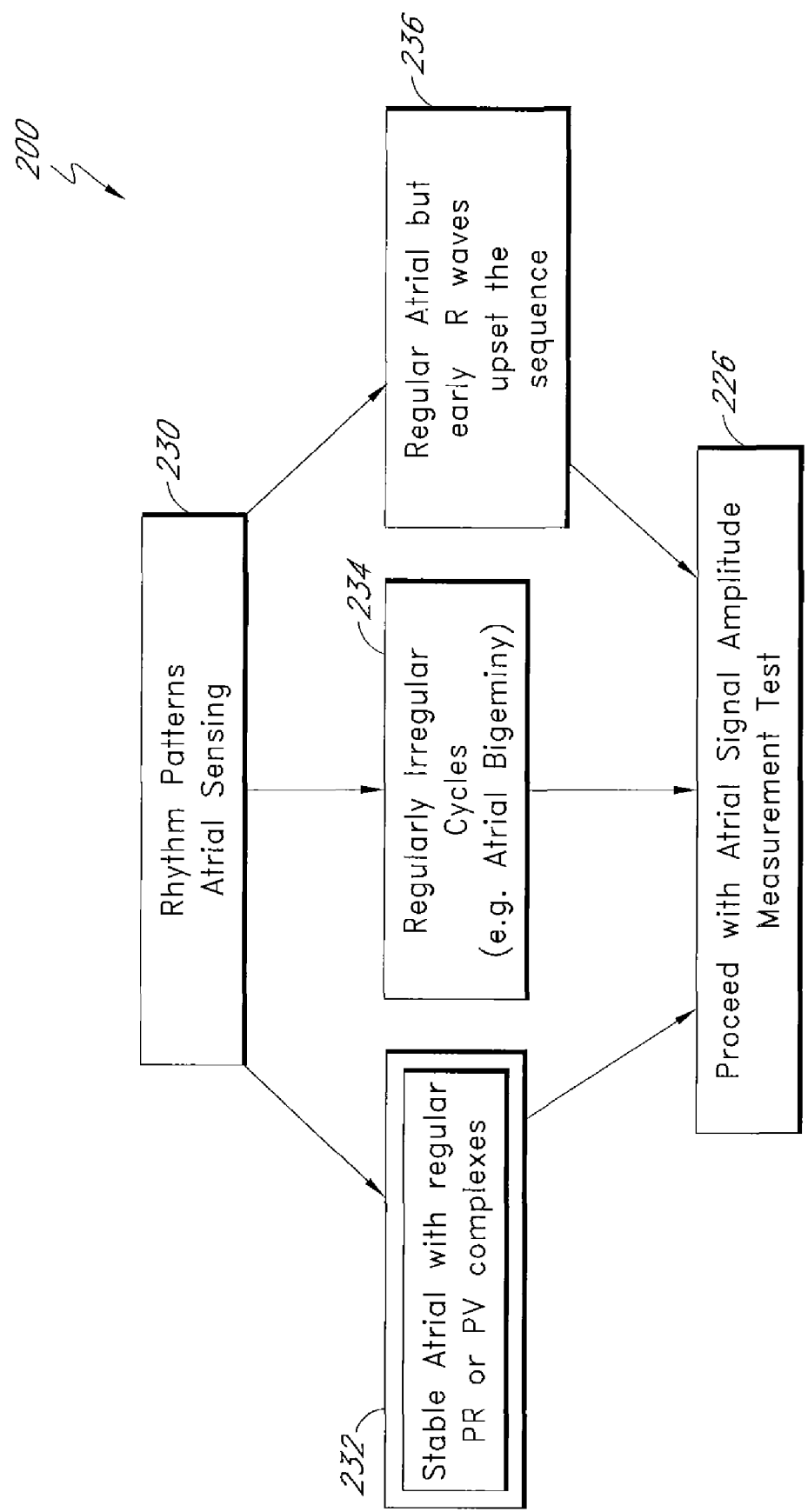
FIG. 8 is a flow chart illustrating exemplary categories of atrial rhythm which the automatic signal measurement test is adapted to accommodate.

FIG. 8 is a flow chart illustrating various possibilities and determinations made by the algorithm 200 in states 222 and 224. In this embodiment, reference is made to evaluation of a physiological process constituting the activity of the patient's atria and corresponding rhythm patterns in state 230. The evaluation of state 230 can lead to numerous possibilities including but not limited to those illustrated in FIG. 8 including a state 232 indicating relatively stable atrial activity with relatively regular PR or PV complexes. State 234 indicates a condition of relatively regular irregular cycles for example a condition of atrial bigeminy. State 236 corresponds to a condition of relatively regular atrial activity but with relatively regularly R waves upsetting the otherwise stable and periodic atrial activity. Of course other characteristic patterns could be determined in state 224 and the nature of the characterized patterns guides the algorithm 200 through the process of the signal amplitude measurement of state 226.

Figure 9:
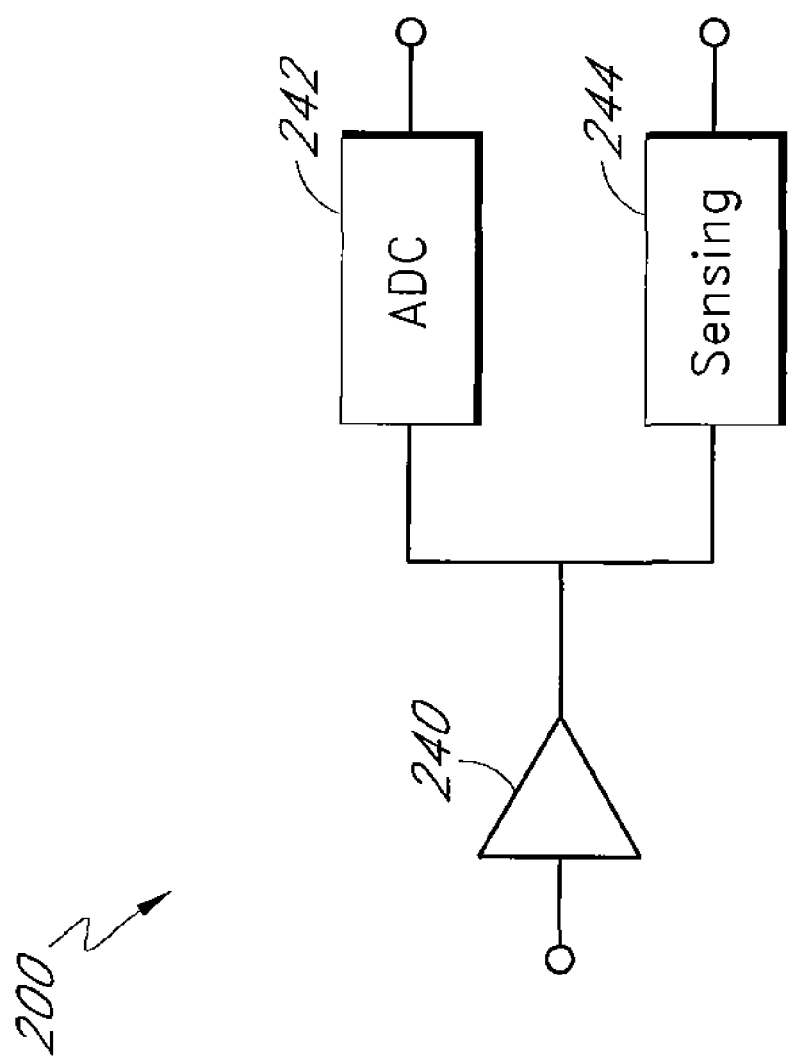
FIG. 9 is a simplified circuit diagram of one embodiment of signal amplifying and sensing components of the implantable device.

FIG. 9 is a simplified circuit diagram of one embodiment of sensing and detection components of the device 10 the setting and adjustment of which is guided by the algorithm 200. In this embodiment, the physiological activity monitored by the device 10 is conducted or communicated to an amplifier 240. The amplifier 240 has variable and adjustable gain and the output of the amplifier 240 is fed to both an analog-to-digital converter (ADC) 242 as well as to a sensing component 244, such as a window comparator. The ADC 242 provides a digitized output, such as an 8 bit value having 256 discreet values. A larger number of bits for the ADC 242 output provides higher resolution of the sensed signals, however at the cost of higher processing capacity and power consumption burden. The sensing component 244 evaluates the output of the amplifier 240 and provides a yes/no or threshold evaluation of the output of the amplifier 240. Thus, the ADC 242 provides a digitized approximation of the analog output of the amplifier 240 while the sensing component 244 provides a threshold determination or simple yes/no evaluation of the same output.

The settings or adjustment of the gain of the amplifier 240 as well as the setting of the threshold regulating the output of the sensing component 244 are preferably set such that the dynamic range of the amplifier 240 and ADC 242 fully encompass the range of the physiological stimulation feeding into the amplifier 240 to avoid saturating the amplifier 240 but also such that the dynamic range is also substantially employed. If the amplifier 240 saturates, the device 10 can infer that the corresponding physiological process has reached a maximum sensed value, however the true peak magnitude of the physiological process is clipped and thus lost as the sensing as communicated to the amplifier 240 and 242 exceeds the adjusted maximum output of these components. However a substantial portion of the dynamic range is also preferably employed such that the available dynamic range is advantageously substantially employed to provide a more precise approximation of the true magnitude of the physiological process.

Thus, the settings of the amplifier 240 and ADC 242 are preferably set so as to avoid this saturation or clipping condition yet are also preferable set relatively aggressively so as to utilize a significant portion of the dynamic range of the amplifier 240 and ADC 242 to provide a higher resolution to the sensing of the physiological process. In a likewise manner, the threshold of the sensing component 244 is also preferably adjusted and set such that a physiological process of interest, such as the previously described occurrences of P waves is reliably detected with reduced occurrences of false positives and false negatives. The settings of the gain of the amplifier 240 as well as the sensing threshold of the sensing component 244 are set according to embodiments of the signal amplitude measurement algorithm 200 as described below with reference to FIGS. 10-12 in a manner that efficiently employs the processing and battery capacity of the device 10.

Figure 10:
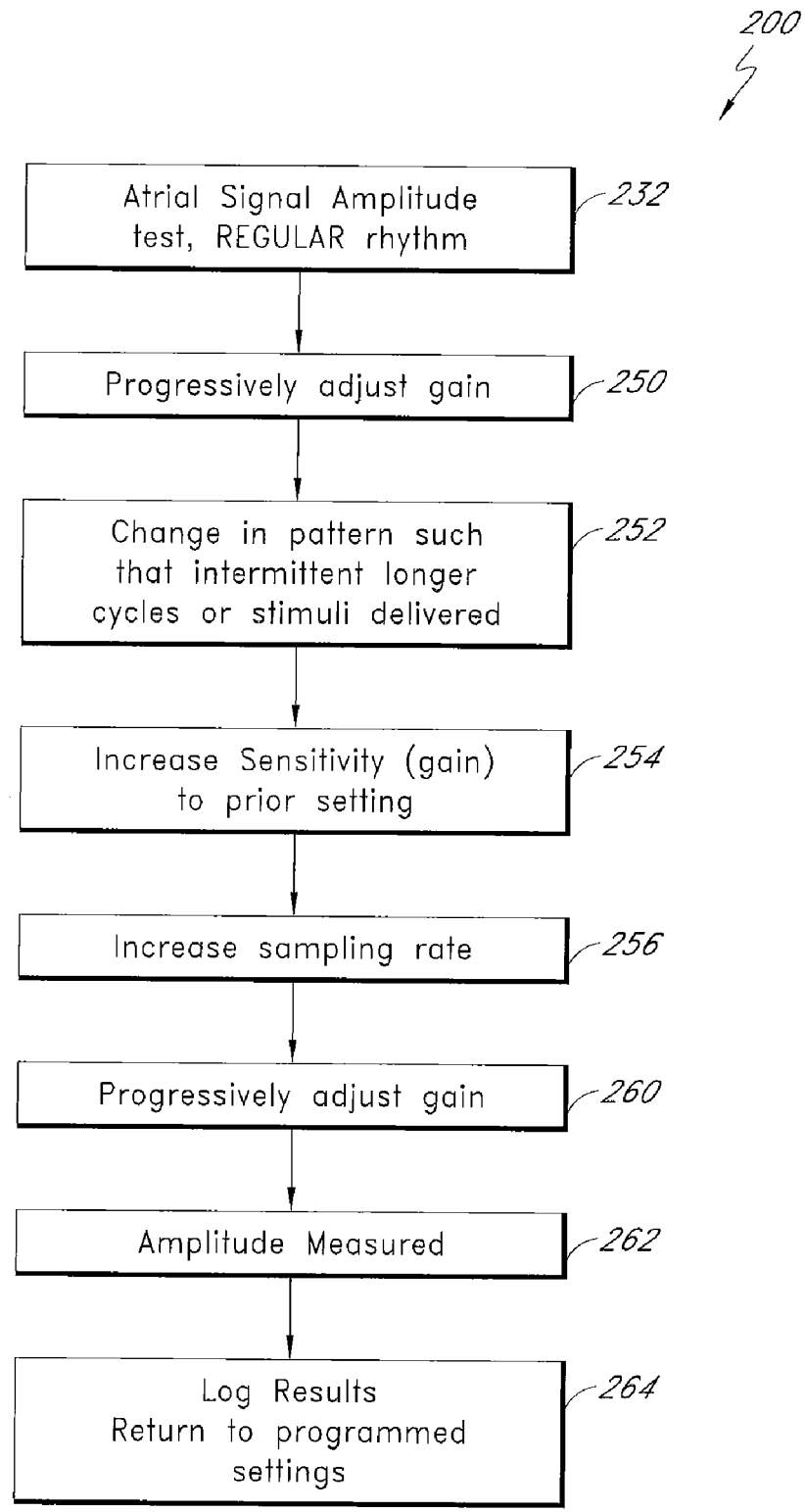
FIG. 10 is a flow chart of one embodiment of an automatic signal measurement test for atrial channels where the rhythm is determined to be relatively regular and simply periodic.

FIG. 10 is a flow chart illustrating one embodiment of the algorithm 200 and more particularly the progression of the algorithm 200 under the determination of state 232 that a relatively stable atrial rhythm is present with relatively regular PR or PV complexes. In this embodiment, the algorithm 200 proceeds to a state 250 with a corresponding evaluation of state 252 wherein the relationship between the gain of the amplifier 240 and the threshold setting is progressively adjusted and the response of the device 10 is evaluated for determination of a change in pattern of observed physiological activity. The algorithm 200 looks for indications that intermittently or more consistently longer cycles of physiological activity are being observed or that the observed activity indicates delivery of therapeutic stimulation to restore physiological function indicating that the device 10 has ceased to properly detect the underlying physiological activity (e.g. is undersensing).

FIGS. 11A-11E illustrate embodiments of the progressive adjustment of gain/threshold and evaluation of the sensing corresponding thereto with respect to a waveform indicative of the sensing performed by the amplifier 240 and sensing of the ADC 242 and sensing component 244. This description and illustration is made with respect to the particular example of the P wave corresponding to the patient's atrial activity and explanation will be made regarding strictly the sensing of the amplitude over time, however it will be understood that the invention encompasses other physiological processes and other aspects of the processes, such as the morphology, timing characteristics, etc.

Figure 11A:
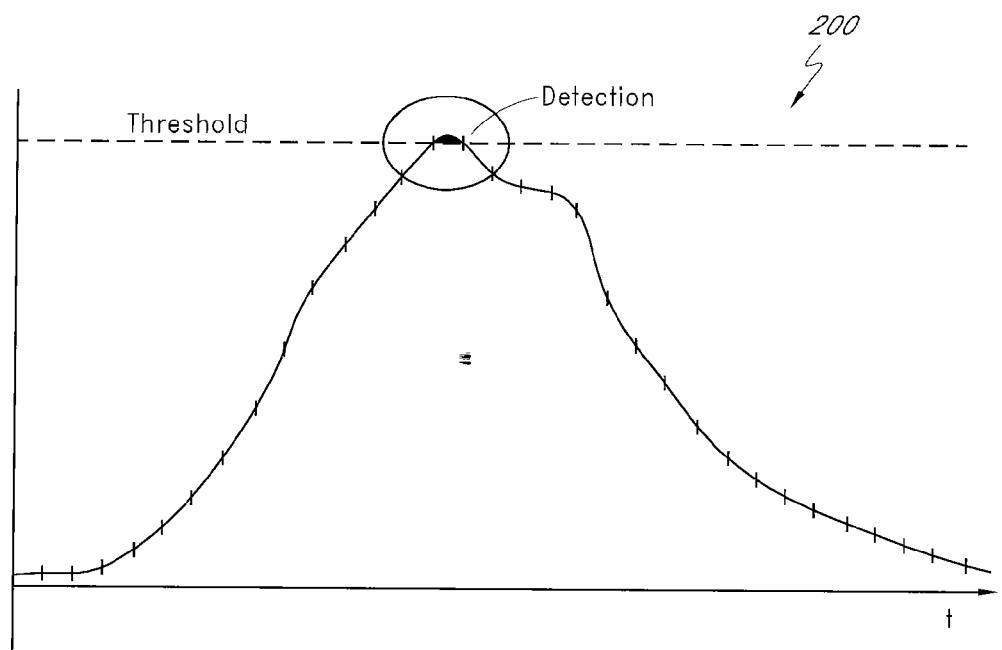
FIGS. 11A-11E illustrate exemplary wave forms evaluated according to embodiments of the automatic signal measurement tests.

FIG. 11A illustrates sensing of the physiological parameter with an initial sensitivity or gain setting indicated by the horizontally extending dashed line labeled threshold. FIG. 11A also indicates a relatively low sampling rate for example at intervals of approximately 4 milliseconds or at 256 Hz. As can be seen in FIG. 11A the physiological parameter exceeds the threshold and thus the device 10 would properly detect the occurrence of this physiological parameter of interest.

Figure 11B:
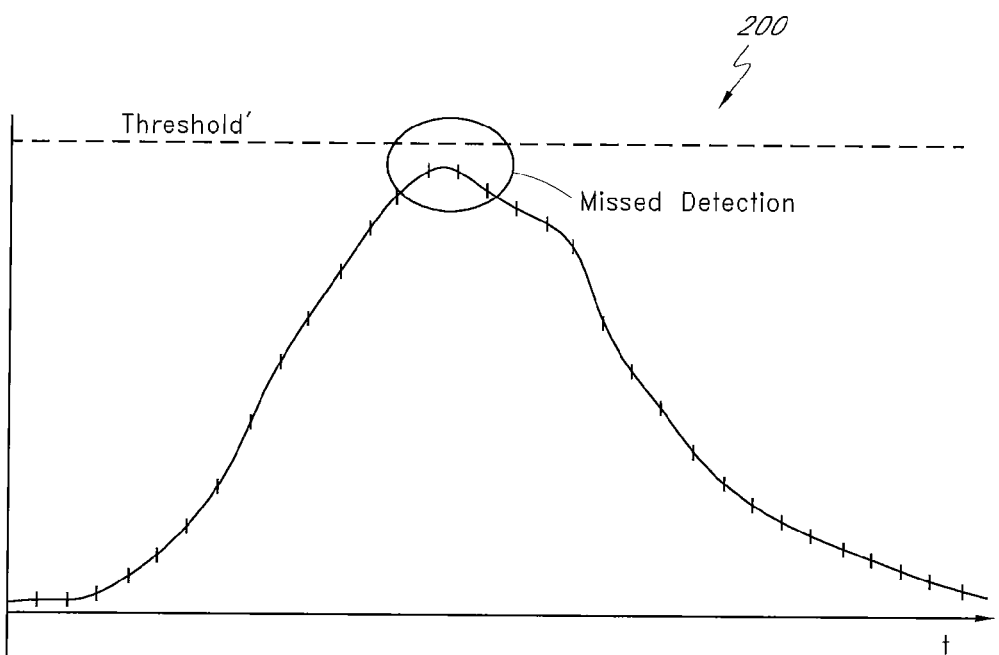

FIG. 11B illustrates a subsequent step in the automatic signal measurement algorithm 200 where either the gain of the amplifier 240 has been adjusted downwards and/or the threshold setting of the sensing component 244 has been adjusted upwards (indicated by threshold') such that the sensed magnitude of the physiological parameter fails to reach the threshold' value and thus the device 10 fails to detect the physiological parameter of interest as occurring although sensing is occurring.

Figure 11C:
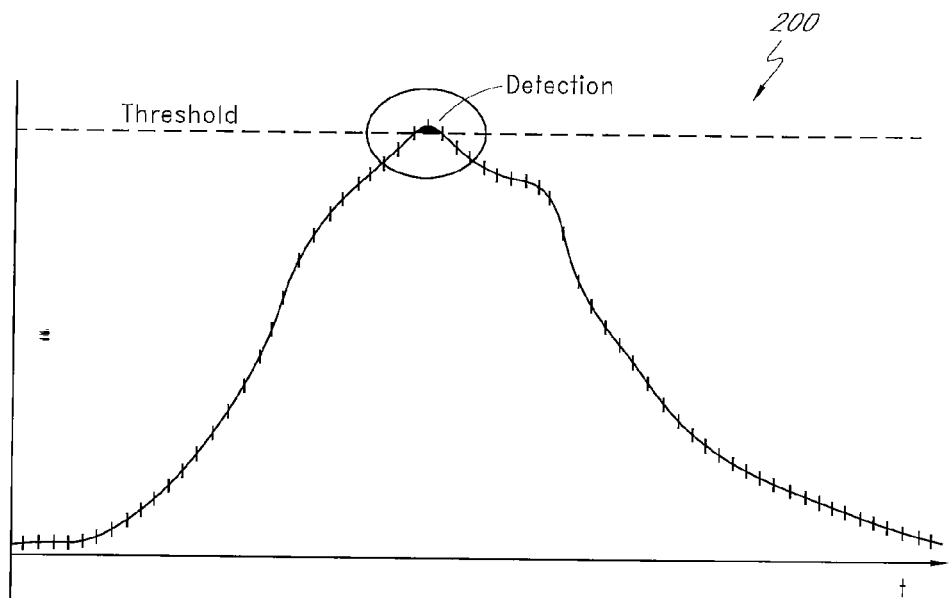

FIG. 11C illustrates a subsequent step indicated in the flow chart of FIG. 10 as states 254 and 256 where the threshold (and/or gain of the amplifier 240) is adjusted back to the previous setting as shown in FIG. 11A and the sampling rate or resolution of the ADC 242 is increased, in this embodiment to a interval of approximately 2 milliseconds or 512 Hz. As shown in FIG. 11C the device 10 again properly detects the physiological parameter and by sampling at an increased rate obtains higher resolution information related to the magnitude of the physiological parameter over time.

Figure 11D:
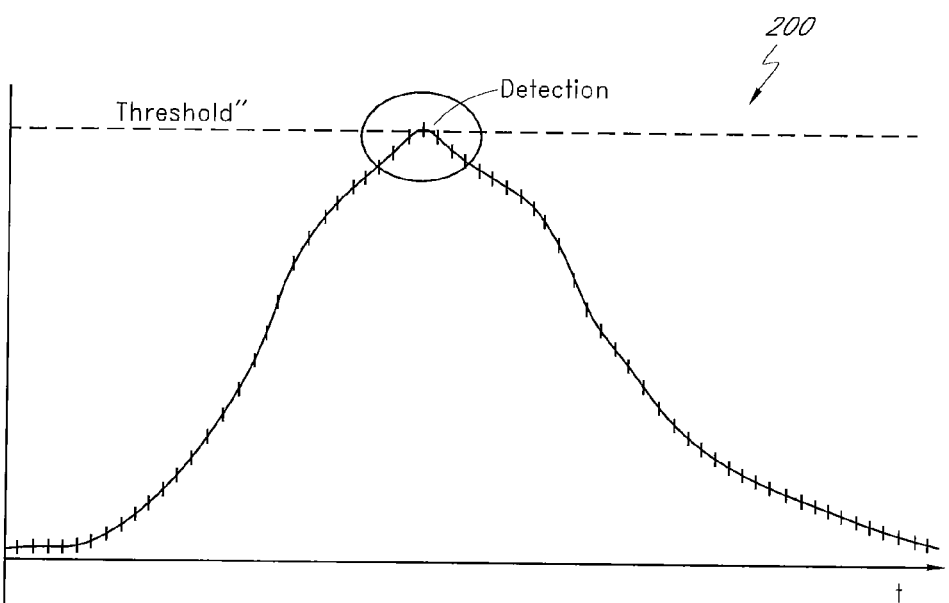

FIG. 11D illustrates a further step in the automatic signal measurement algorithm 200 also indicated in the flow chart of FIG. 10 as states 260 and 262 where the threshold setting is again adjusted as indicated by threshold' and as shown the device 10 does detect the physiological parameter and because of the higher rate sampling obtains a higher resolution or more precise valuation of the peak magnitude of the physiological parameter.

Figure 11E:
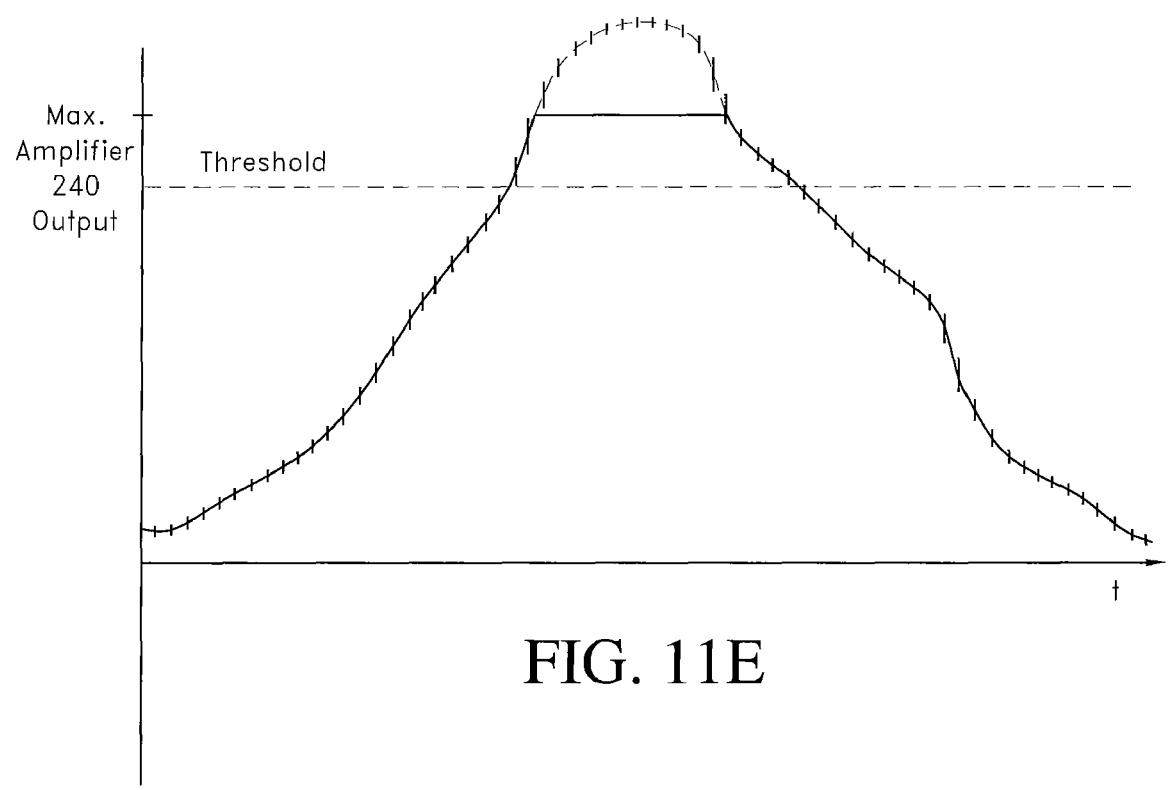

FIG. 11E is a graphic illustration of steps in the algorithm 200 wherein the gain of the amplifier 240 is adjusted and determined to be adjusted too high. In particular, FIG. 11E illustrates that the true magnitude of the sensed physiological process is of sufficient magnitude (indicated by the broken lines of the waveform) as to exceed the dynamic range of the amplifier 240 as adjusted. The setting of the threshold is such that detection occurs, but data corresponding to the true peak magnitude of the physiological process is lost as the output of the amplifier 240 and the ADC 242 reaches a maximum value. The algorithm 200 can determine this occurrence by observing a period of constant, maximum output of the amplifier 240 and ADC 242 as the underlying physiological process would not normally be expected to maintain a constant magnitude for an extended period of time. A result of the algorithm such as illustrated by FIG. 11E would indicate a reduction in the gain of the amplifier 240 to avoid this clipping and loss of data.

As will be understood, this process can be repeated in an iterative manner a number of times according to the particular application and desire for measurement resolution as well as subject to the limitations of available processing and battery capacity. In one embodiment, upon completion of these processes in state 264, the results of the test are recorded and the device 10 returns to the previously programmed settings and ongoing device operation as previously described. In certain embodiments, the device 10 can reprogram itself with an improved set of sensing parameters determined from the test.

It will be understood that the results of the signal amplitude measurement algorithm 200 can be used both as evaluative data communicated to a clinician for evaluation of the performance and therapy provided by the device 10 as well as a control variable for determination of appropriate programming of the device 10. One advantage of the signal amplitude measurement algorithm 200 is reduced need for the more demanding higher rate sampling. In particular, the device 10 employing the algorithm 200 incrementally increases the sampling rate as needed, however begins at a relatively low rate and gathers valuable information with lower demands on processing and battery capacity by the lower rate sampling which provides initial data to develop rough information which higher rate sampling can further refine.

Figure 12:
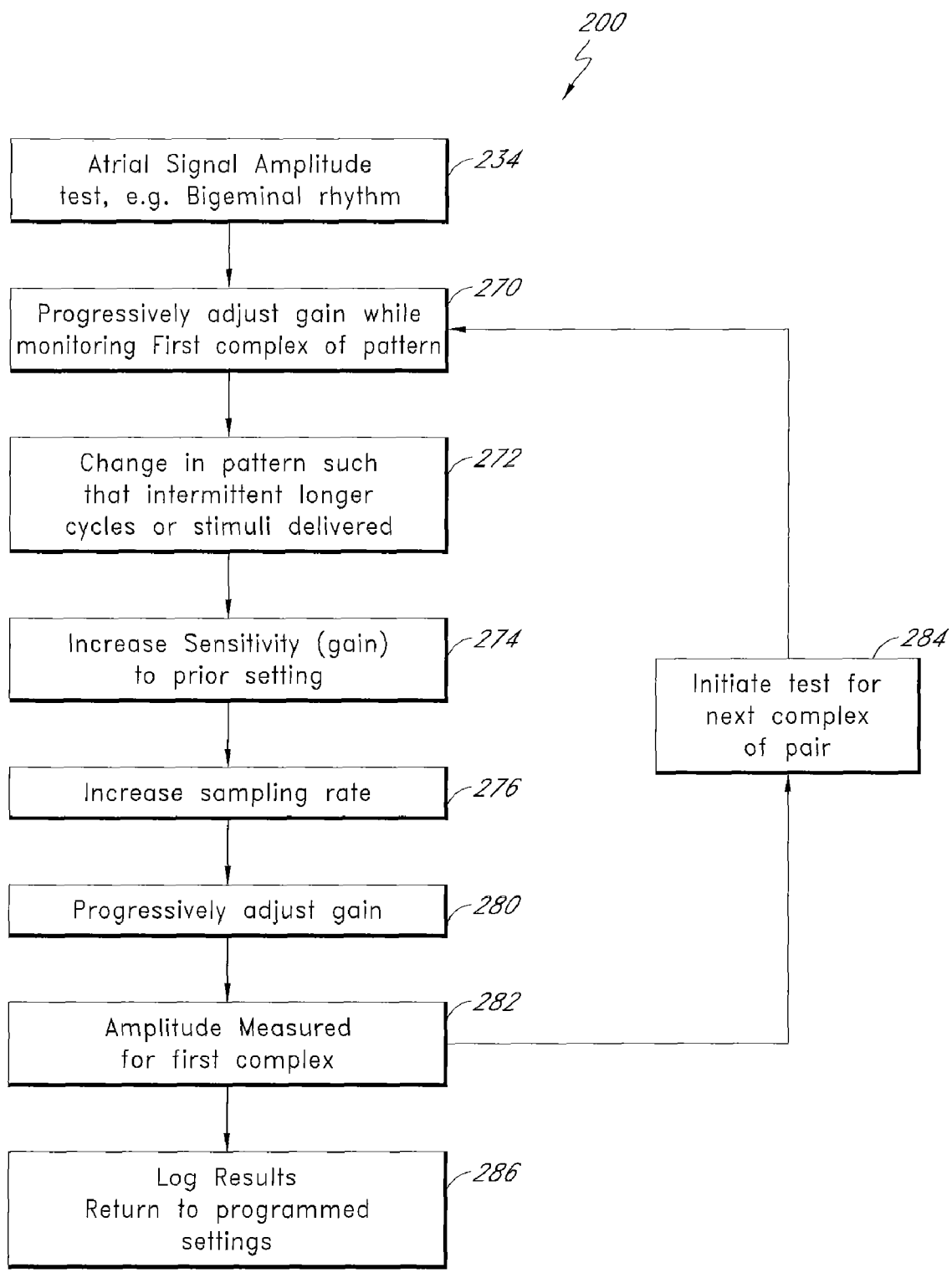
FIG. 12 is a flow chart of one embodiment of an automatic signal measurement test for atrial channels where the rhythm exhibits repetition of an irregular pattern.

FIG. 12 illustrates a further embodiment of the signal measurement amplitude algorithm 200 and more particularly those embodiments indicated by state 234 characterized by cardiac activity of a generally regular irregularity, such as bigeminy or trigeminy. In this embodiment, the algorithm 200 proceeds similarly as previously described, however with the further refinement of evaluating distinct complexes embodied within the regularly irregular pattern.

Thus in states 270 and 272 the algorithm 200 proceeds to progressively adjust the gain and monitors the detection of the first complex as previously described for states 250 and 252 with any absence of detection being indicated by delivery by the device of therapeutic stimulation to restore the physiological activity which the device 10 has failed to detect. Similarly, in states 274, 276, 280, and 282 the algorithm 200 iteratively adjusts the sensitivity and re-evaluates the detection of the physiological process and repeats these measurements at higher sampling rates as indicated in a similar manner to that previously described for states 254, 256, 260, and 262.

Upon completion of the measurement for the first complex of the pattern, the algorithm proceeds via state 284 to repeat the states 270, 272, 274, 278, 280, and 282 for the next complex of the pattern. This process is repeated a number of times corresponding to the number of distinct complexes designated by the algorithm 200 to more accurately determine appropriate threshold setting for a physiological process exhibiting the noted relatively regular repetition of an irregular or not simply periodic pattern. Similarly as previously described for state 264, in state 286 the results of the algorithm 200 are recorded in memory and/or utilized for adjustment of the programmed settings of the device 10 as indicated.

In these embodiments, the number of cycles or occurrences of the physiological process of interest upon which the signal measurement algorithm 200 is performed can be predefined as well as be a programmable value which may have a default value, for example three cycles. Thus, in embodiments where the physiological process is relatively regular as in state 232, the algorithm 200 can be performed for three cycles which may or may not be successive cycles.

Figure 13:
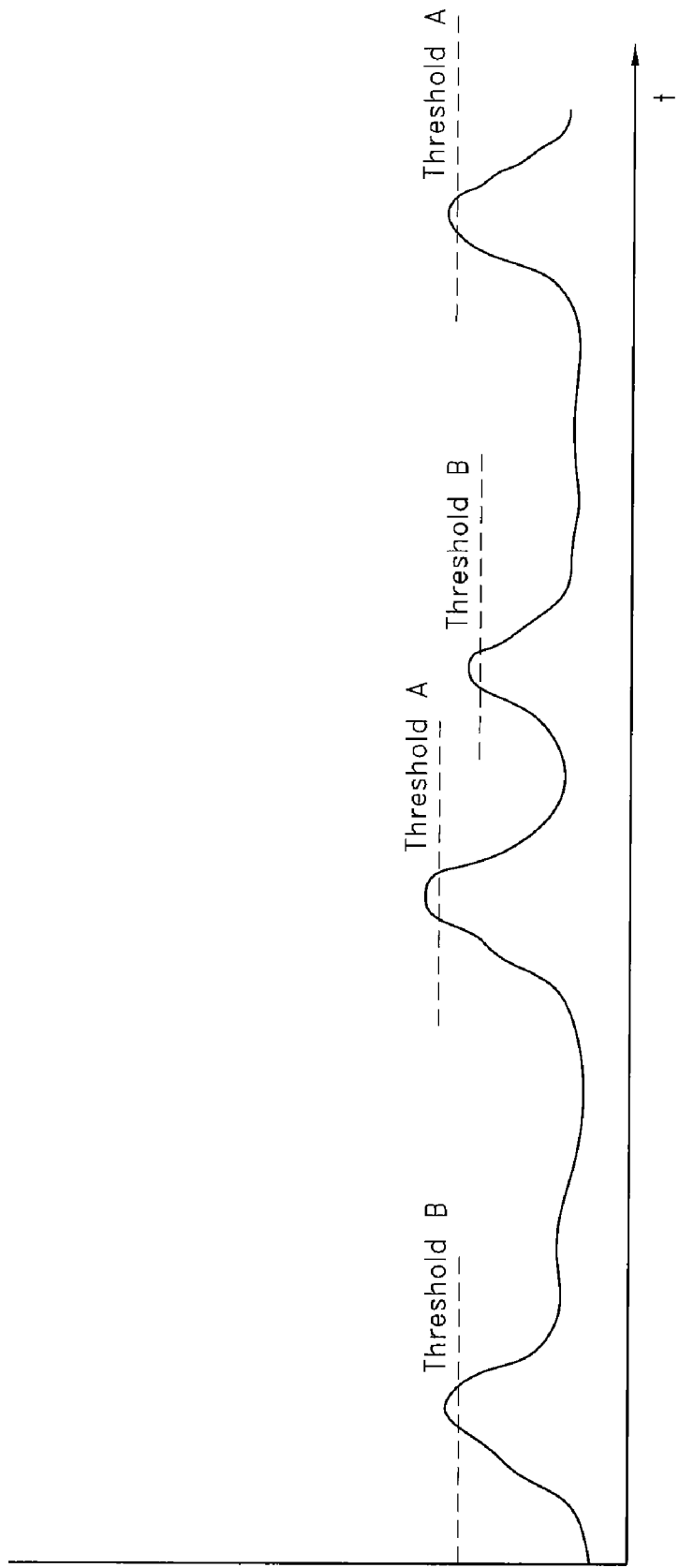
FIG. 13 is a waveform of a repetitive, but not strictly periodic, waveform with corresponding threshold/gain settings for the different complexes of the repetitive waveform.

In embodiments wherein the physiological process exhibits a relatively regular irregularity, such as a condition of bigeminy, the algorithm 200 would be conducted for a similar number of cycles encompassing the repeated pattern. Thus, for example in embodiments exhibiting bigeminy, a repetition of three cycles of the measurement would encompass three pairs or six individual cycles of the physiological process of interest. It will also be appreciated that in the embodiments of irregularity or regular irregularity of the physiological process, the algorithm 200 can determine and report different sensitivity measurements corresponding to the different incidences of the physiological process. The device 10 can thus establish different gain/threshold settings for the different complexes in the repetitive patterns as shown in FIG. 13 as threshold A and threshold B.

It will also be appreciated that the algorithm 200 can be employed in a quasi-real time or on the fly basis as well as being performed upon stored date from previously sensed signals such as made in states 264 and 286. Thus, the determination of failure to detect a given physiological process, such as an atrial depolarization, can be performed in a virtual manner by indication for delivery of therapeutic stimulation without the requirement for actual delivery of this stimulation. It will be further appreciated that in embodiments wherein the physiological process is regular but periodically or intermittently disrupted by other factors, such as a pattern of relatively regular atrial activity which is upset by early occurrence of ventricular activity, the algorithm 200 can generate or adjust blanking periods as well as disregard the sensed signals occurring within such circumstances.

Although the above disclosed embodiments of the present teachings have shown, described and pointed out the fundamental novel features of the invention as applied to the above-disclosed embodiments, it should be understood that various omissions, substitutions, and changes in the form of the detail of the devices, systems and/or methods illustrated may be made by those skilled in the art without departing from the scope of the present teachings. Consequently, the scope of the invention should not be limited to the foregoing description but should be defined by the appended claims.

What is claimed is:

1. An implantable medical device comprising:
an implantable sensing electrode;
a variable gain sense amplifier in communication with the sensing electrode so as to receive signals sensed therefrom; and
a controller in communication with the sensing electrode via the variable gain amplifier wherein the controller is configured to: monitor the signals received from the sensing electrode; detect the occurrence of physiological processes based on the signals exceeding a programmable threshold value; and periodically perform an automatic sensing test; wherein to perform the sensing test the controller is configured to evaluate the sensed signals; characterize a pattern thereof; and if the pattern comprises a repetition of an irregular complex including at least two different individual complexes, then for each individual complex, iteratively temporarily reprogram sensing parameters to a more aggressive setting until undersensing of the individual complex occurs and establish an effective set of sensing parameters for the individual complex corresponding to the last set of sensing parameters for which undersensing of the individual complex did not occur.

2. The device of claim 1, wherein the sensing parameters comprise at least one of the gain of the amplifier and the programmable threshold value defining the detection and wherein the more aggressive settings comprise at least one of a lowering of the amplifier gain and an increase in the threshold value.

3. The device of claim 1, wherein a repetition of an irregular complex comprises a bigeminous atrial rhythm.

4. The device of claim 1, wherein the controller is configured to: initially perform the automatic sensing test at a first, lower sampling rate; and, upon completion of the automatic sensing test at the first sampling rate, repeat the test at least once more at a second, higher sampling rate.

5. The device of claim 1, further comprising a telemetry circuit configured to communicate with an external device and telemetrically report results of the testing to the external device, wherein the controller is configured to induce periodic testing of the sensing of the device upon receipt of a command from the external device.

6. The device of claim 1, wherein the controller is further configured to monitor for indications that the amplifier is saturating by being configured to monitor for sensing the physiological process as occurring at a constant, maximum value.

7. An implantable medical device comprising:
a processor programmed with an initial set of sensing parameters including at least one of an amplifier gain and a detection threshold in the device; and
electrodes adapted to sense a signal indicative of at least one physiological process;
wherein the processor is operative to:
evaluate the signal over time to determine whether the signal comprises a repetition of an irregular complex including at least two different individual complexes;
for each individual complex, determine a set of sensing parameters by automatically self-adjusting at least one of the amplifier gain lower and the detection threshold higher until undersensing of the individual complex occurs and establish an effective set of sensing parameters for the individual complex corresponding to the last set of sensing parameters for which undersensing of the individual complex did not occur.

8. The device of claim 7 wherein the signal is a cardiac electrogram and the irregular complex is bigeminy.

9. The device of claim 8 wherein a first individual complex corresponds to a first depolarization in the bigeminy pair and a second individual complex corresponds to a second depolarization in the bigeminy pair.

10. The device of claim 7 wherein the processor is further operative to, upon undersensing of an individual complex, and prior to establishing an effective set of sensing parameters:
set the sensing parameters so that undersensing does not occur; and
repeat, at a higher sampling rate, the automatic self-adjusting of the sensing parameters until undersensing of the individual complex occurs.

* * * * *